(12) United States Patent
Smith et al.

(10) Patent No.: US 10,051,869 B2
(45) Date of Patent: Aug. 21, 2018

(54) COMPOSITIONS AND METHODS FOR IMPROVING PLANT HEALTH

(71) Applicants: Gregory R. H. Smith, Ontarion (CA); Eric Davies, Raleigh, NC (US)

(72) Inventors: Gregory R. H. Smith, Ontarion (CA); Eric Davies, Raleigh, NC (US)

(73) Assignee: HSC Organics LLC, Apollo Beach, FL (US)

( * ) Notice: Subject to any disclaimer, the term of this patent is extended or adjusted under 35 U.S.C. 154(b) by 0 days.

(21) Appl. No.: 14/756,088

(22) Filed: Jul. 28, 2015

(65) Prior Publication Data
US 2017/0027178 A1     Feb. 2, 2017

(51) Int. Cl.
| | |
|---|---|
| *A01N 63/02* | (2006.01) |
| *A01N 43/84* | (2006.01) |
| *A01N 63/00* | (2006.01) |
| *A01N 61/00* | (2006.01) |
| *C05F 3/00* | (2006.01) |
| *C05F 11/08* | (2006.01) |
| *C05F 17/00* | (2006.01) |

(52) U.S. Cl.
CPC ............ *A01N 63/02* (2013.01); *A01N 43/84* (2013.01); *A01N 61/00* (2013.01); *A01N 63/00* (2013.01); *C05F 3/00* (2013.01); *C05F 11/08* (2013.01); *C05F 17/0018* (2013.01); *Y02A 40/205* (2018.01); *Y02P 20/145* (2015.11)

(58) Field of Classification Search
CPC ........ A01N 63/02; A01N 43/84; A01N 63/00; A01N 61/00; C05F 3/00; C05F 11/08; C05F 17/0018
See application file for complete search history.

(56) References Cited

U.S. PATENT DOCUMENTS

| | | | | |
|---|---|---|---|---|
| 2002/0053229 | A1* | 5/2002 | Varshovi | C05D 9/00 71/6 |
| 2002/0103083 | A1* | 8/2002 | Harman | A01N 63/04 504/117 |
| 2015/0257383 | A1* | 9/2015 | Deisenroth | A01N 37/12 504/100 |

FOREIGN PATENT DOCUMENTS

| | | | | |
|---|---|---|---|---|
| WO | WO-0246126 A1 | * | 6/2002 | ............. C05F 3/00 |
| WO | WO 2013/152337 A1 | * | 10/2013 | ............. C05D 9/02 |

OTHER PUBLICATIONS

Baumgartner, K., and Warnock, A. E. 2006. A soil inoculant inhibits Armillaria mellea in vitro and improves productivity of grapevines with root disease. Plant Disease. 90:439-444.*
Norman Q. Arancon and Clive A. Edwards. 2005. Effects of Vermicomposts on Plant Growth. Paper presented during the International Symposium Workshop on Vermi Technologies for Developing Countries (ISWVT 2005), Los Banos, Philippines Nov. 16-18, 2005.*
Jeanine I. Boulter, Greg J. Boland, and Jack T. Trevors, "Assessment of compost for suppression of Fusarium Patch (*Microdochium nivale*) and Typhula Blight (*Typhula ishikariensis*) snow molds of turfgrass", Biological Control 25 (2002) 162-172.*
Jeanine I. Boulter, Jack T. Trevors and Greg J. Boland, "Microbial studies of compost: bacterial identification, and their potential for turfgrass pathogen suppression", World Journal of Microbiology & Biotechnology 18: 661-671, 2002.*
Jeanine I. Boulter, Greg J. Boland, and Jack T. Trevors, "Evaluation of Composts for Suppression of Dollar Spot (*Sclerotinia homoeocarpa*) of Turfgrass", Plant Disease, 2002, 86:405-410.*
Eric B. Nelson and Michael J. Boehm, "Compost-Induced Suppression of Turf Grass Disease", BioCycle, 2002, 51-55.*

* cited by examiner

*Primary Examiner* — John Pak
*Assistant Examiner* — Nathan W Schlientz

(57) ABSTRACT

Disclosed are compositions and methods for preparing compositions that improve plant health and reduce fungal infestations. Also disclosed are methods of using the compositions described herein to improve plant health by applying the compositions directly to plants, and/or applying the compositions to substrates used for plant growth. The compositions include a synergistic ratio of composting bacteria, bio-surfactant producing bacteria, bio-remediating bacteria, bovine feces, and humic acid. The compositions reduce fungal growth and fungal infestation the infected area. Methods of reducing brown patch and/or dollar spot infestations to a plant such as turf grass or crop are also described herein.

12 Claims, 2 Drawing Sheets

COMPOSITIONS AND METHODS FOR IMPROVING PLANT HEALTH

FIELD OF THE INVENTION

The present invention relates generally to the field of compositions and methods for treatment of plants such as turf grass and related species of flora, and, more particularly, to the field of improvements of compositions and methods for improving health of turf-grass and other flora especially when subject to fungal infection.

BACKGROUND

Plants, including turf-gasses, live in an often-hostile environment, where they are subject to many stressors including heat, cold, drought, flooding and attack by pests such as insects and fungi. Many different fungi infect grass roots, causing their death. These fungi include *Basidiomycetes* and *Ascomycetes*. The most visible are the fruiting bodies of *Basidiomycetes*, the well-known mushrooms and puffballs. The fungal infections they cause are often called fairy rings and mini-rings. Other *Basidiomycetes* cause an array of fungal diseases, including so-called rust, root rot, *Rhizoctonia* diseases of turf grass, stinking smut, and others. These fungi are more difficult to identify, because they rarely if ever have their fruiting stage, which is the diagnostic anatomical test for fungi. Currently even experts have difficulty identifying them, and the only secure way is to do genomic analysis. Nevertheless, all these fungi are typically given the generic name *Rhizoctonia*. The second major group of fungi is *Ascomycetes*, which are even less well characterized. They cause diseases such as anthracnose of turf grass, dollar spot of turf grass, (caused by *Sclerotinia homoeocarpa*), early blight of potato and tomato, and others.

The majority of plants, including turf grass, especially when under stress, such as frequent mowing, extreme temperatures, drought, flooding, etc., becomes prone to fungal infections. These are proving difficult and expensive to control. It has been shown that the dark green circles in turf grass fields are from fungi colonizing the soil, leaf litter, thatch, or emanating from buried wood products. These fungi can sometimes cause the development of spots, rings or arcs of deep green grass or circles of dead grass, which may vary in size.

The most common fungi affecting the most sensitive (and valuable) turf grass swards are mycelium fungi attacking golf greens and the most common means of control is by toxic chemical fungicides. For example, on golf greens, the main fungal infestations are the result of thatch-dwelling and/or thatch—utilizing mycelium fungi. As with the majority of agents that kill (for example, toxic chemical fungicides), the rapidly growing organisms (for example, fungal mycelium) typically develop resistance. This is happening, for example, with some of the main fungicides used on golf courses, such as TARTAN®, PROSTAR 70WG®, TRINITY®, INSIGNIA®, and others.

The bulk of the fungus-evoked damage to golf greens results from the activity of mycelium fungi which: a) live in and utilize the thatch layer as their major food source. Removal of the food source would deplete the nutrition available to the fungi, thus lessen their abundance and thus the severity of damage inflicted on the turf; b) kill the fungi by secreting toxins and poisons; and c) make the soil hydrophobic, thus lessening the ability of the plants to take up water and nutrients. Since these are all saprophytic fungi (i.e., they cannot colonize living plants, they must kill them first, hence getting rid of the toxins would lessen fungal ability to attack the plant roots.

There have been many approaches to solve the problem of fungal infections. Some of them involve thatch management efforts, including changing the soil pH, and core aerating to remove thatch and enhance its breakdown and to permit water and air movement. Other efforts include the use of pesticides, fumigation of infected turf areas, removing portions of the infected soil, and applying nitrogen to mask the symptoms of infection, by causing the rest of the lawn to green up. None of these previous methods have been shown to be completely effective or environmentally friendly.

As the public pushes for organic environmental solutions, turf managers have found it challenging to maintain visually-pleasing, healthy turf while being environmentally friendly. Brown patch, yellow patch, fairy ring, and compacted and hydrophobic soils challenge soil and turf management practices. Despite the desire to reduce fungal growth, there are no really effective biological products to protect turf against fungal infestations. It is desirable to make turf care effective and simple at the same time, by reducing fungal infestation and controlling the growth of fungi using biological methods, in an environmentally friendly manner. It would be advantageous to invent compositions and methods that overcome these deficiencies as well as improving plant health. The present invention addresses these and related needs.

BRIEF SUMMARY

The present technology relates generally to compositions and methods for treatment of the growing environment (e.g., soil environment) of plants such as turf grass and related species of flora, which compositions and methods can be used for improving plant health.

According to one aspect of the invention, a composition is provided for improving plant health. The composition includes a synergistic ratio of composting bacteria, bio-surfactant producing bacteria, bio-remediating bacteria, bovine feces, and humic acid. Preferably, the synergistic ratio is approximately $10^4$ to $10^{12}$ CFU (colony-forming units) per ml for each bacterial species, approximately between 1% and 25% (w/v) bovine feces, and approximately between 0.01% and 1.00% (w/v) humic acid. More preferably, the synergistic ratio is approximately between $10^6$ and $10^{10}$ CFU per ml for each bacterial species, approximately between 5% and 15% (w/v) bovine feces, and approximately between 0.1% and 0.75% (w/v) humic acid. Most preferably, the synergistic ratio is approximately $10^8$ CFU per ml for each bacterial species, approximately, approximately 10% (w/v) bovine feces, and approximately 0.5% (w/v) humic acid. The composition of the present invention preferably includes: composting bacteria that comprise *Nocardioides kongjuensis, Clostridium phytofermentans, Clostridium cellulolyticum, Comamonas jiangduensis, Comamonas testosteroni*, and *Bacillus subtilis*; bio-surfactant producing bacteria that comprise *Comamonas jiangduensis, Comamonas testosteroni*, and *Pseudomonas aeruginosa*; and toxin remediating bacteria that comprise *Pseudomonas pseudoalcaligenes, Pseudomonas putida, Pseudomonas fluorescens*, and *Comamonas testosteroni*.

In another aspect, the invention provides a method that comprises providing fungi-infested plant with a composition comprising a synergistic ratio of (i) composting bacteria, (ii) bio-surfactant producing bacteria, (iii) bio-remediating bacteria, (iv) bovine feces, and (v) humic acid. Preferably, the synergistic ratio is approximately $10^4$ to $10^{12}$ CFU (colony-forming units) per ml for each bacterial species, approximately between 1% and 25% (w/v) bovine feces, and approximately between 0.01% and 1.00% (w/v) humic acid. More preferably, the synergistic ratio is approximately between $10^6$ and $10^{10}$ CFU per ml for each bacterial species, approximately between 5% and 15% (w/v) bovine feces, and approximately between 0.1% and 0.75% (w/v) humic acid. Most preferably, the synergistic ratio is approximately $10^8$ CFU per ml for each bacterial species, approximately, approximately 10% (w/v) bovine feces, and approximately 0.5% (w/v) humic acid. Preferably, the composition includes: composting bacteria that comprise *Nocardioides kongjuensis, Clostridium phytofermentans, Clostridium cellulolyticum, Comamonas jiangduensis, Comamonas testosteroni,* and *Bacillus subtilis*; bio-surfactant producing bacteria that comprise *Comamonas jiangduensis, Comamonas testosteroni,* and *Pseudomonas aeruginosa*; and toxin remediating bacteria that comprise *Pseudomonas pseudoalcaligenes, Pseudomonas putida, Pseudomonas fluorescens,* and *Comamonas testosteroni*.

According to another aspect, a method of improving plant health is provided. The method includes providing plant growth substrate with a composition comprising a synergistic ratio of (i) composting bacteria, (ii) bio-surfactant producing bacteria, (iii) bio-remediating bacteria, (iv) bovine feces, and (v) humic acid. Preferably, the synergistic ratio is approximately $10^4$ to $10^{12}$ CFU (colony-forming units) per ml for each bacterial species, approximately between 1% and 25% (w/v) bovine feces, and approximately between 0.01% and 1.00% (w/v) humic acid. More preferably, the synergistic ratio is approximately between $10^6$ and $10^{10}$ CFU per ml for each bacterial species, approximately between 5% and 15% (w/v) bovine feces, and approximately between 0.1% and 0.75% (w/v) humic acid. Most preferably, the synergistic ratio is approximately $10^8$ CFU per ml for each bacterial species, approximately, approximately 10% (w/v) bovine feces, and approximately 0.5% (w/v) humic acid. Preferably, the composition includes: composting bacteria that comprise *Nocardioides kongjuensis, Clostridium phytofermentans, Clostridium cellulolyticum, Comamonas jiangduensis, Comamonas testosteroni,* and *Bacillus subtilis*; bio-surfactant producing bacteria that comprise *Comamonas jiangduensis, Comamonas testosteroni,* and *Pseudomonas aeruginosa*; and toxin remediating bacteria that comprise *Pseudomonas pseudoalcaligenes, Pseudomonas putida, Pseudomonas fluorescens,* and *Comamonas testosteroni*.

According to an additional aspect of the invention, the plant whose health is improved is any type of plant, including monocots and dicots. Preferably, the plant whose health is improved is turf grass. In yet another aspect of the invention, the composition is provided to a plant or a plant part, or to the proximity thereof. In some embodiments, the composition is provided to a plant substrate in which the plant is planted.

Not wanting to be bound by the following theory, the novel composition works by changing the soil environment so the plant thrives and the fungus does not. It is the synergistic combination of the three kinds of bacteria (composting bacteria, bio-surfactant producing bacteria, and bio-remediating bacteria) in combination with bovine feces and humic acid. The composting bacteria get rid of thatch (which is fungal food), the bio-surfactant producing bacteria get rid of hydrophobicity, and the bio-remediating bacteria get rid of fungus-produced toxins. The inventors used their decades of experience in plant biology to make this discovery and reduce it to practice.

The foregoing is a summary and thus by necessity contains simplifications, generalizations and omissions of detail. Consequently, those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

DETAILED DESCRIPTION OF THE PRESENTLY PREFERRED EMBODIMENTS

Figure 1:
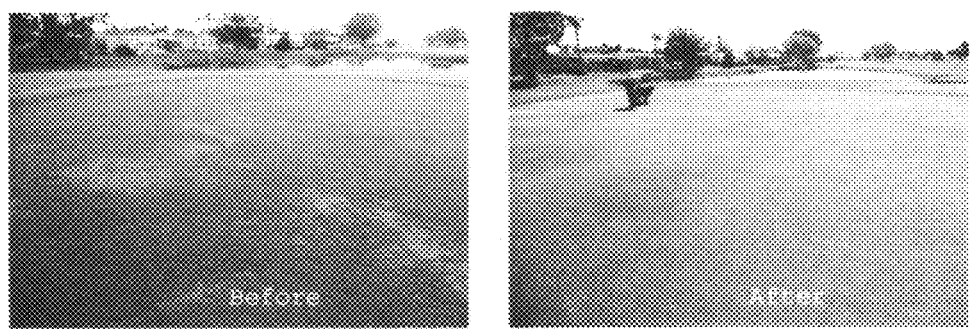
FIG. 1 photographically shows the detrimental effects of fungal infection on turf grass at a golf course (see left panel, labeled "Before"), and the beneficial effects of the composition of the present invention (i.e., same plot treated with the composition, see right panel, labeled "After").

In the following detailed description, numerous specific details are set forth to provide a thorough understanding of the concepts underlying the described embodiments. It will be apparent, however, to one skilled in the art that the described embodiments can be practiced without some or all of these specific details. In other instances, well known process steps have not been described in detail in order to avoid unnecessarily obscuring the underlying concepts.

Broadly speaking the embodiments herein describe a new approach, which relates to compositions and methods for reducing fungal infestation and improving the health of grass. More particularly, the invention is concerned with the control, reduction, or elimination of undesirable fungal infections of turf grass, especially of high quality turf grass that is used in home lawns, parks, sporting fields (e.g., soccer, baseball, football, etc.), golf fairways, and golf greens. In accord with the present invention, the reduction in fungal infestation is typically associated with improvement in the grass quality.

The disadvantages listed above with current techniques (e.g., toxic chemicals, environmentally unsound, repeated application of chemical surfactants to make the soil less hydrophobic) are severe, expensive and short-lived. Accordingly the inventors developed a totally novel approach, which utilizes a newly developed mix of bacteria. These bacteria can be listed as 3 main types: a) those that decompose plant matter (i.e. remove fungal food sources, so the fungi die of starvation and also remove the thatch layer so water and air can penetrate to the plant roots; b) those that make bio-surfactants on a continuing basis (i.e., reverse soil hydrophobicity in the absence of frequently added chemicals and thereby enabling the plant roots to take up existing water and nutrients (without the need of supplying extra fertilizer); and c) those that degrade fungal toxins so the fungi cannot invade them saprophytically (i.e., prevent death of grass). In one aspect of the inventions, the inventors were especially interested in bacteria that would degrade a major toxin (cyanide) produced by many fairy ring fungi. To develop the compositions of the present invention, the inventors looked at two major sources of bacteria: a) those commercially available bacteria, with known composting and other useful properties; and b) those retrievable from dried fecal matter from different herbivores, especially ruminants, and more specifically cow dung.

Exemplary bacterial genera useful in the practice of the present invention include but are not limited to: *Acinetobacter, Bacillus, Clostridium, Comamonas, Nocardioides,* and *Pseudomonas*.

Exemplary bacterial species useful in the practice of the present invention include but are not limited to: *Acinetobacter* sp. nov. *Bacillus subtilis, Clostridium cellulolyticum, Clostridium phytofermentans, Comamonas jiangduensis, Comamonas testosteroni, Nocardioides kongjuensis, Pseudomonas plecoglossicida,* and *Pseudomonas pseudoalcaligenes*.

The bacteria used in the practice of the invention can be obtained from a variety of sources. The sources include, but are not limited to: (1) composting solutions: *Acinetobacter* spp., *Clostridium phytofermentans, Clostridium cellulolyticum, Comamonas jiangduensis, Comamonas testosteroni,* and *Pseudomonas pseudoalcaligenes*; and 2) cow manure: *Bacillus subtilis, Nocardioides kongjuensis,* and *Pseudomonas plecoglossicida*.

The inventors surprisingly discovered that at least three types of bacteria are needed for maximal efficacy in alleviating the stress brought about by fungal infestation in a range of plant species including golf green turf grasses: (1) those that produce plant cell wall degrading enzymes, such as cellulase, ligno-cellulase, and pectinase. These are referred to as "composting bacteria". Furthermore, since the fungus-infected soils are often short of oxygen (despite frequent aeration), the composting bacteria must include those that are aerobic, anaerobic and facultative anaerobic with each varying in efficacy as the soil conditions ameliorate during treatment; (2) those that produce bio-surfactants which render the soil less hydrophobic and make conditions less suitable for the fungi and more suitable for the plants to take up water and nutrients. These are "bio-surfactant producing bacteria" (or "hydrophilic-making bacteria"); and (3) those that break down toxins including HCN and others produced by fungi to kill the plants. These are referred to as "toxin remediating bacteria" or "bio-remediating bacteria", and are frequently also producers of bio-surfactants.

The composting bacteria, bio-surfactant producing bacteria and remediating bacteria can be obtained, for example, from cattle (e.g., cow) manure, and from composting treatments.

The bacterial complement of cow manure may vary with the breed of cattle (e.g., cow), the time of year and the region where they are raised. As well, the bacterial complement of composting solutions may vary by region and time of year, thus the specific bacteria might vary from batch to batch. Nevertheless, each batch of the compositions of the present invention contains an appropriate required bacterial mix comprising a minimum of three composting bacteria, one bio-surfactant producing bacterium, and one remediating bacterium.

Exemplary composting bacteria useful in the practice of the present invention include but are not limited to: *Nocardioides kongjuensis, Clostridium phytofermentans, Clostridium cellulolyticum, Comamonas jiangduensis, Comamonas testosteroni,* and *Bacillus subtilis*.

Exemplary bio-surfactant producing bacteria useful in the practice of the present invention include but are not limited to: *Comamonas jiangduensis, Comamonas testosteroni,* and *Pseudomonas aeruginosa*.

Exemplary toxin remediating bacteria useful in the practice of the present invention include but are not limited to: *Pseudomonas pseudoalcaligenes, Pseudomonas putida, Pseudomonas fluorescens,* and *Comamonas testosteroni*.

Not wanting to be bound by the following explanation, the embodiments herein describe a new approach, which is to alleviate the conditions brought about by the fungus and, rather than attempt to kill the fungus, sway the ecological balance in favor of the plant (for example, grass). With fairy ring fungi especially (for example, *Agaricus* ssp. and *Marasmius oreades*), the main negative effect of the fungi is to create a massive water resistant mycelial mat, and for many of the over 60 fungal species, to secrete both toxins and hydrophobic compounds. Combined with the death of the plants caused by the fungal toxins, the hydrophobic conditions prevent the surviving plants from taking up water and nutrients; the plants cannot take up water so readily and nutrient availability is compromised.

According to one aspect of the invention, a composition is provided for reducing fungal infestation. The composition includes a synergistic ratio of composting bacteria, bio-surfactant producing bacteria, bio-remediating bacteria, bovine feces, and humic acid. Preferably, the synergistic ratio is approximately $10^4$ to $10^{12}$ CFU (colony-forming units) per ml for each bacterial species, approximately between 1% and 25% (w/v) bovine feces, and approximately between 0.01% and 1.00% (w/v) humic acid. More preferably, the synergistic ratio is approximately between $10^6$ and $10^{10}$ CFU per ml for each bacterial species, approximately between 5% and 15% (w/v) bovine feces, and approximately between 0.1% and 0.75% (w/v) humic acid. Most preferably, the synergistic ratio is approximately $10^8$ CFU per ml for each bacterial species, approximately 10% (w/v) bovine feces, and approximately 0.5% (w/v) humic acid.

In another aspect, the invention provides a method that comprises providing fungi-infested plant with a composition comprising a synergistic ratio of (i) composting bacteria, (ii) bio-surfactant producing bacteria, (iii) bio-remediating bacteria, (iv) bovine feces, and (v) humic acid. Preferably, the synergistic ratio is approximately $10^4$ to $10^{12}$ CFU (colony-forming units) per ml for each bacterial species, approximately between 1% and 25% (w/v) bovine feces, and approximately between 0.01% and 1.00% (w/v) humic acid. More preferably, the synergistic ratio is approximately between $10^6$ and $10^{10}$ CFU per ml for each bacterial species, approximately between 5% and 15% (w/v) bovine feces, and approximately between 0.1% and 0.75% (w/v) humic acid. Most preferably, the synergistic ratio is approximately $10^8$ CFU per ml for each bacterial species, approximately, approximately 10% (w/v) bovine feces, and approximately 0.5% (w/v) humic acid. Preferably, the composition includes: composting bacteria that comprise *Nocardioides kongjuensis, Clostridium phytofermentans, Clostridium cellulolyticum, Comamonas jiangduensis, Comamonas testosteroni,* and *Bacillus subtilis*; bio-surfactant producing bacteria that comprise *Comamonas jiangduensis, Comamonas testosteroni,* and *Pseudomonas aeruginosa*; and toxin remediating bacteria that comprise *Pseudomonas pseudoalcaligenes, Pseudomonas putida, Pseudomonas fluorescens,* and *Comamonas testosteroni*.

According to another aspect, a method of improving plant health is provided. The method includes providing plant growth substrate with a composition comprising a synergistic ratio of (i) composting bacteria, (ii) bio-surfactant producing bacteria, (iii) bio-remediating bacteria, (iv) bovine feces, and (v) humic acid. Preferably, the synergistic ratio is approximately $10^4$ to $10^{12}$ CFU (colony-forming units) per ml for each bacterial species, approximately between 1% and 25% (w/v) bovine feces, and approximately between 0.01% and 1.00% (w/v) humic acid. More preferably, the synergistic ratio is approximately between $10^6$ and $10^{10}$ CFU per ml for each bacterial species, approximately between 5% and 15% (w/v) bovine feces, and approximately between 0.1% and 0.75% (w/v) humic acid. Most preferably, the synergistic ratio is approximately $10^8$ CFU per ml for each bacterial species, approximately, approximately 10% (w/v) bovine feces, and approximately 0.5% (w/v) humic acid. Preferably, the composition includes: composting bacteria that comprise *Nocardioides kongjuensis, Clostridium phytofermentans, Clostridium cellulolyticum, Comamonas jiangduensis, Comamonas testosteroni*, and *Bacillus subtilis*; bio-surfactant producing bacteria that comprise *Comamonas jiangduensis, Comamonas testosteroni*, and *Pseudomonas aeruginosa*; and toxin remediating bacteria that comprise *Pseudomonas pseudoalcaligenes, Pseudomonas putida, Pseudomonas fluorescens*, and *Comamonas testosteroni*.

The compositions and methods of the present invention are effective for reducing infestations by fungi such as *Basidiomycetes* and *Ascomycetes*. This invention is particularly useful in reducing infestations of thatch-dwelling and/or thatch—utilizing mycelium fungi.

Improving plant health and reducing fungal infestation, the compositions and methods of the present invention are useful for improving the growth and quality of all grasses tested including a variety of both cool-season grasses and warm-session grasses. Cool-season grasses include grasses that utilize C3 photosynthesis. These include, for example, tall fescue, fine fescue, Kentucky bluegrass, and perennial ryegrass. Warm-season grasses include grasses that utilize C4 photosynthesis. These include but are not limited to Bermuda-grass, Centipede-grass, Zoysia-grass, and Augustine-grass, and salt-grass (*Paspalum vaginatum*).

Not wanting to be bound by the following explanation, there seem to be at least three different ways of helping fungus-infected greens, and preferably golf greens. One approach is killing the fungus, for example using bacteria, as described, for example, in U.S. Pat. No. 6,444,614. Another approach is stimulating the plant directly, so that it is more resistant to the fungus, for example using bacteria to stimulate the plants, as described, for example, in U.S. Pat. No. 6,995,007. The inventors have surprisingly discovered that there is a third way of helping fungus-infected greens, and preferably golf greens, for example, modifying the plant environment with a soil amendment.

In accordance with the present invention it has been unexpectedly discovered that (i) composting bacteria, (ii) bio-surfactant producing bacteria, (iii) bio-remediating bacteria, (iv) bovine feces, and (v) humic acid are synergistically effective in reducing the growth of fungi while simultaneously enhancing plant health. The combination of the three different kinds of bacteria, bovine feces, and humic acid shows a greater inhibitory effect on fungal growth and enhanced improvement of plant health in excess of composting bacteria, bio-surfactant producing bacteria, bio-remediating bacteria, bovine feces, or humic acid alone.

The term "composting bacteria" refers to those bacteria found naturally in composting situations and those present in cow manure as well as those deliberately introduced to aid in composting and are gram negative or gram positive, rod-shaped or cylindrical, motile or non-motile. Some of the composting bacteria include strains that have great resistance to anti-bacterial soaps and detergents and can digest organic matter such as dead plant material, turf thatch, oils and grease. Composting bacteria may be found in certain commercial compositions that are used in making plant compost. They synthesize and secrete enzymes (such as cellulase and pectinase) that degrade the cell wall materials in the thatch layer thus depriving the infesting fungi of a food supply and making the soil more water and air permeable so the plants benefit.

In some preferred embodiments, composting bacteria useful in the practice of this invention are *Acinetobacter* sp., *Pseudomonas* sp. and *Comamonas* sp. More preferably, composting bacteria useful in the practice of this invention are *Acinetobacter plecoglossicida, Pseudomonas plecoglossicida, Comamonas testosteroni, Comamonas jiangduensis, Nocardioides kongjuensis* and *Staphylococcus warneri*.

The term "bovine feces" refers to the waste product of bovine animal species, and includes but is not limited to cow dung, cow pats, cow pies, cow manure, or bovine dung. These bovine animal species include but are not limited to domestic cattle ("cows"), bison ("buffalo"), yak, and water buffalo. Bovine feces are the undigested residue of plant matter which has passed through the animal's gut. The resultant fecal matter is rich in bacteria with similar properties to those found in commercial composting mixtures (described above) that degrade dead vegetative material. Bovine feces color ranges from greenish to blackish, often darkening soon after exposure to air. Bovine feces of the present invention are preferably obtained from animals that have not been fed antibiotics. The bovine feces used in the practice of this invention is preferably partially aged and decomposed.

In preferred embodiments of the present invention, dried bovine feces is used as one of the ingredients, preferably in the amount of 100 kilograms of dry bovine feces per 1000 liters of final composition volume of 10% (w/v).

Bovine feces may also contain bacteria. Some bacteria, such as *Pseudomonas* sp., for example, may be present in the compositions of the present invention both in the bovine feces, and also as composting bacteria.

The term "humic acid" refers to the principal component of humic substances, which are the major organic constituents of soil (humus), peat, coal, many upland streams, dystrophic lakes, and ocean water. The terms "humic substances", "humates", "humic acids" and "humus" are often used interchangeably in the industry of agriculture. Humic acid is produced by biodegradation of dead organic matter. It is not a single acid; rather, it is a complex mixture of many different acids containing carboxyl and phenolate groups so that the mixture behaves functionally as a dibasic acid or, occasionally, as a tribasic acid. Humic acids can form complexes with ions that are commonly found in the environment creating humic colloids. Humic and fulvic acids (fulvic acids are humic acids of lower molecular weight and higher oxygen content than other humic acids) can be used as a soil supplement in agriculture. Accordingly, the term "humic acid" is meant to expressly include fulvic acid, as both humic acid and fulvic acid can be interchangeably used in the practice of the present invention. Humic substances such as humic acid are in nature formed by the microbial degradation of dead plant matter, such as lignin.

A typical humic substance is a mixture of many molecules, some of which are based on a motif of aromatic nuclei with phenolic and carboxylic substituents, linked together. The functional groups that contribute most to surface charge and reactivity of humic substances are phenolic and carboxylic groups. Humic acids behave as mixtures of dibasic acids, with a pK value around 4 for protonation of carboxyl groups and around 8 for protonation of phenolate groups. There is considerable overall similarity among individual humic acids. For this reason, measured pK values for a given sample are average values relating to the constituent species. The humic acids in this invention are typically soluble humic acids.

The term "reduction in fungal infestation" or "reducing fungal infestation" refers to the decrease and/or inhibition of fungal growth and is intimately linked with improved plant health. When the plant is turf, the term "reduction in fungal infestation" or "reducing fungal infestation" refers to the decrease and/or inhibition of fungal growth and is intimately linked with improved turf health.

Figure 2:
FIG. 2 photographically shows the detrimental effects of fungal infection on turf grass at a golf course (see left panel, labeled "Before"), and the beneficial effects of the composition of the present invention (i.e., same plot treated with the composition, see right panel, labeled "After").

The reduction in fungal infestation and improvement in plant health may be partial or complete. Within the scope of the present invention, reduction in fungal growth and improvement in turf (or any other plant) health refers to the reduction in the percentage of killed or damaged turf (unhealthy—brown or yellow) compared with the total turf area (unhealthy brown or yellow plus healthy green) turf. To do this, the photographs such as in FIG. 1-3 are printed on equal weight paper, the seriously infested region cut out (brown, yellow and green) and weighed, then the unhealthy areas (brown and yellow) and healthy areas (green) are cut out and weighed separately. For instance, if the total region (brown, yellow, green) is 100% (or 100 grams for easy calculation) and the unhealthy (brown, yellow) area is 60% (60 grams) so the proportion of infected (damaged, unhealthy) area is 60% of the total region in the "Before treatment" of FIG. 1A. The % unhealthy areas drops to 3% of the total region in "After treatment" in FIG. 1B. Thus the unhealthy area drops from 60 grams to 3 grams and furnishes a 60/3 or 20-fold (2000%) decrease in the unhealthy area. Such detailed analyses are not required by golf course superintendents, however, as upon application of products that act to reduce fungal infestation they can easily see the vast improvements of grass health and the golf players report major increase in playability of the greens and keep coming back to the treated courses.

The compositions and method of the present invention can be used for the reduction of fungal infestation and improvement of plant health on a variety of substrates that are infected with fungi. They are preferably useful for the treatment and reduction of fungal growth of fungi-infected plants and soils, and are useful in agriculture, such as for example, for application to a golf field or to an area of grass infected with fungi, to suppress and/or control the growth of the fungi and improve plant health. More preferably, they can be used for the treatment of fungi-infected turf grass.

In one aspect of the invention methods for the reduction of undesirable fungal infections and improvement of plant health include providing a synergistic ratio of composting bacteria, bovine feces, and humic acid to a fungus-infested substrate. The substrate may include, but is not limited to, plant growing media, plant growing substrates, soil, artificial soil, mineral wool, or any mixtures thereof.

The invention is particularly useful for reduction of fungal infestation of turf grass grown on golf courses or grass grown on lawns or lawns, meadows, sport fields or sport grounds, or pitches.

The invention is particularly useful for improvement of the health of turf grass grown on golf courses or grass grown on lawns, meadows, sport fields or sport grounds, or pitches.

In one preferred embodiment, the composition of the present invention includes the following ingredients, for a 1,000 liter tank: (i) composting bacteria, $10^8$ CFU/ml, biosurfactant-producing bacteria, $10^8$ CFU/ml, and toxin-degrading (remediating) bacteria, $10^8$ (note that each group of the three groups of bacteria is used at a concentration of approximately $10^8$ CFU/ml), (ii) bovine feces, approximately 100 kg of dry weight, and (iii) humic acid, approximately 5 kg. To obtain the composition of the present invention, the above ingredients are solubilized and diluted with water up to 1,000 liters to create a mixture.

The above mixture is then incubated for varying periods of time, preferably between approximately one week and approximately twenty weeks, more preferably between approximately two weeks and approximately sixteen weeks, and most preferably approximately eight weeks.

The incubation temperatures may vary, and they are preferably between approximately 1° C. and approximately 45° C., more preferably between approximately 10 and approximately 40° C., and most preferably approximately 25° C. to 35° C.

In one embodiment of the invention, after incubation at the preferred temperature, the mixture is filtered, preferably one to five times, and more preferably three times, using strainers generally known in the art. The strainer hole size is typically approximate to the size of spaghetti strainers (first straining—larger hole), then medium hole (second straining), and then small hole (third straining—angel hair pasta size), although the size may vary. The strainers are used to remove particulate matter so the spray hoses do not clog up. Generally, the filtered composition of the present invention needs to be of sufficient clarity and viscosity for liquid applications, for example to pass through the spray rig nozzles that are typically used in the art, e.g. those used for the treatment of golf courses or in other agricultural applications.

Humic acid useful in the practice of the present invention can be used as salt, e.g., Mg-humate, K-humate, as humic acid derivatives, etc. In the preferred composition of the present invention, the amount of humic acid may vary, and it is preferably between approximately 0.5 kg and 25 kg per 1,000 liters of total mixture, more preferably between 2 kg and 12.5 kg per 1,000 liters of total mixture, and most preferably approximately 5 kg per 1,000 liters of total mixture.

The composition of the present invention can be used immediately after preparation and incubation, i.e. it can be applied as soon as the ingredients are mixed, incubated and filtered. Preferably the ingredients are filtered, to obtain filtered liquid for ease of application. Alternatively, the composition of the present invention can be stored for a period of time before use. For example, the composition can be stored for approximately up to two years without significant decrease in effectiveness. The storage temperature is preferably between 1° C. and 45° C., more preferably between 10° C. and 40° C., and most preferably between 25° C. and 35° C.

The above concentrations describe the production of a batch of 1,000 liters of composition of the present invention. Of course, one skilled in the art will know how to scale up or scale down the production, and the manufacture any desired amount of the composition.

Once the composition is obtained, incubated, and filtered, it can be directly used and applied for purposes of treatment of the plant/soil environment. Preferably, however, the composition is used as a concentrate that is further diluted for application purposes. For example, the final (working) concentration is preferably diluted 1-100 fold, more preferably 5-50 fold, and most preferably 15-25 fold. In other words, 1,000 liters of mixture can be diluted 20-fold to yield a 20,000 liters working solution for application purposes.

The phrase "improving plant health" refers to control of fungal growth and/or reduction in fungal infestation, which according to the present invention refers to at least 50%, more preferably 75%, more preferably 95%, and most preferably 100% reduction in fungal growth in comparison to untreated plant control sample. The comparison can be conducted in a variety of ways, e.g. by measuring the areas of soil surface where the dead turf grass gets turned into more than 90% live grass, by measuring the ratio of green turf grass vs. yellow turf grass (comparing the brown and green areas in photographs), or by using quantitative data for plant growth known in the art, such as chlorophyll fluorescence.

The phrase "providing the composition of the present invention" refers to the application of the composition of the present invention to desired substrate or object, for example directly to the plant/soil environment. The composition is particularly effective on soils where years of accumulation of thatch generate conditions suitable for the fungal growth.

The phrase "proximity" refers to a term well understood in the art. For example, proximity refers to the application of the composition of the present invention sufficiently close to the planks), so that the control of fungal growth and/or reduction in fungal infestation is effected in accordance with this invention. Proximity also refers to the subsequent "watering in" which enables the product to reach the thatch layer for maximum effect.

The composition of the present invention can be applied to a variety of fungi-infected plants and/or fungi-infected substrates alone, or in conjunction with other substances. For example, the composition can be applied to plants and/or soils in conjunction with fertilizer, but that is usually not required as the treatment enhances the plant's ability to take up the existing fertilizer. For example, the fungi whose deleterious effect can be reduced with two or more treatments in one month and monthly treatments thereafter include but are not limited to all of the fungi listed herein.

Application of the working solution can be achieved in a number of ways. Even though often times even a single application results in substantial reduction in fungi and improvement of plant growth, often times the application is performed periodically, to increase the beneficial antifungal effect. In one example, turf grass used in golf courses can be treated once a week for four weeks, and then every four weeks thereafter until the ground freezes.

Preferred amounts of the composition of the present invention used for the treatment of high value golf greens are approximately 20 liters per hectare. For other sports turf (e.g., golf fairways, soccer fields, baseball fields, football fields), approximately 5 liters of the composition per hectare are used. For ornamental turf (e.g., parks, landscaped facilities, home lawns and generally any maintained grass) the amounts used are approximately 2 liters of composition per hectare of treated area. For severe infestations these numbers can be doubled until the infestation is under control. For agricultural crops, the preferred amounts are approximately 1 liter of the composition per hectare.

Treatment methods depend on several factors; some of those factors include the degree of fungal infestation, for example the age of the fungal ring, soil type, and, moisture content of the soil. Typically, in the case of fungal rings, the infected ring and surrounding soil is watered. The amount of the composition of the invention applied is dependent on the size of the ring. The composition may be applied as is with or without dilution. Application methods include, without limitation, drenching, hose-end sprayers, foliar application, through irrigation, or aerial.

Once applied, the composition of the invention may be watered in to the desired depth. Typically, it needs to be watered in to get the composition to the thatch layer. Should subsequent (second, third, fourth, etc.) applications be desired, the application methods may be simply repeated. The applications methods may be identical, or they may vary, in accord with application methods known in the art.

The addition of an admix is also possible without changing the efficacy of the compositions of the present invention. In some preferred embodiments, the compositions may include carbon sources, minerals, carbohydrates, proteins, sugars, plant growth regulators, amino acids, N-P-K fertilizers, surfactants, algicides such as Copper Sulfate and related copper salts, etc. With this information, further alternative formulations could be formulated that are believed to be similarly effective.

For their practical application, the compounds or compositions of the invention used according to this invention may be part of formulations, which are known in the art.

The compositions comprising the compounds of the present invention can contain other ingredients, for example protective colloids, adhesives or thickeners, thixotropic agents, stabilizers or sequestrants, complexing agents, as well as other active materials.

The compositions useful in the practice of this invention may be formulated in a wide range of forms known to those skilled in the art. The compositions useful in the practice of this invention may, for example, be in the form of a concentrate to be diluted prior to application, or it may be in the form of a granule, powder or liquid with a suitable solid or liquid carrier. Thus, for example, compositions useful in the practice of this invention may be in the form of emulsions, or aqueous dispersions, and may include solvents. In the alternative, the compositions useful in the practice of this invention may be adapted to form an emulsion prior to use.

The compositions useful in the practice of this invention can be prepared in the form of wettable powders, soluble powders, dusting powders, granulates, solutions, emulsifiable concentrates emulsions, suspended concentrates or aerosols, or in microencapsulated form (produced, for example, via coacervation) for controlled release application to plants.

Formulations comprising the compositions of the present invention may be applied to plants by conventional methods including seed application techniques, as well as foliar methods. Preferably, the compositions are applied to plants (and their environment) that grow in soil with a thatch layer as fungal food source. In addition, the compositions of the present invention may be applied to plants indirectly, via application to the substrate used for plant growth. For example, the compositions of the present invention may be applied to soil in which the plant is grown. If the plant is infested with one or more types of fungi, providing such plant with the compositions of the present invention should improve the plant's health. Any of these methods may be used in the practice of the present invention, which essentially comprises applying the inventive compositions to plants and/or plant parts and/or seeds and/or soils to suppress or control fungi in plants, thereby improving plant health.

The invention further contemplates equivalents to the compositions and the methods described above. For example, combining an excess of one component to change the mole ratios would still have the benefit of the present invention. Therefore, the invention is not restricted to the preferred embodiments described and illustrated but covers all modifications and equivalents.

Exemplary Preferred Embodiments

Embodiment 1

A composition for improving plant health, the composition comprising a synergistic ratio of (i) composting bacteria, (ii) bio-surfactant producing bacteria, (iii) bio-remediating bacteria, (iv) bovine feces, and (v) humic acid.

Embodiment 2

The composition of embodiment 1, wherein the synergistic ratio is approximately between $10^4$ to $10^{12}$ colony-forming units (CFU) per ml for each bacterial species, approximately between 1% and 25% (w/v) bovine feces, and approximately between 0.01% and 1.00% (w/v) humic acid.

Embodiment 3

The composition of embodiment 1, wherein the synergistic ratio is approximately between $10^6$ and $10^{10}$ CFU per ml for each bacterial species, approximately between 5% and 15% (w/v) bovine feces, and approximately between 0.1% and 0.75% (w/v) humic acid.

Embodiment 4

The composition of embodiment 1, wherein the synergistic ratio is approximately $10^8$ CFU per ml for each bacterial species, approximately 10% (w/v) bovine feces, and approximately 0.5% (w/v) humic acid.

Embodiment 5

The composition of embodiment 1, wherein the composting bacteria comprise *Nocardioides kongjuensis*, *Clostridium phytofermentans*, *Clostridium cellulolyticum*, *Comamonas jiangduensis*, *Comamonas testosteroni*, and *Bacillus subtilis*.

Embodiment 6

The composition of embodiment 1, wherein the bio-surfactant producing bacteria comprise *Comamonas jiangduensis*, *Comamonas testosteroni*, and *Pseudomonas aeruginosa*.

Embodiment 7

The composition of embodiment 1, wherein the toxin remediating bacteria comprise *Pseudomonas pseudoalcaligenes*, *Pseudomonas putida*, *Pseudomonas fluorescens*, and *Comamonas testosteroni*.

Embodiment 8

The composition of embodiment 1, wherein the composting bacteria comprise *Nocardioides kongjuensis*, *Clostridium phytofermentans*, *Clostridium cellulolyticum*, *Comamonas jiangduensis*, *Comamonas testosteroni*, and *Bacillus subtilis*; the bio-surfactant producing bacteria comprise *Comamonas jiangduensis*, *Comamonas testosteroni*, and *Pseudomonas aeruginosa*; and the toxin remediating bacteria comprise *Pseudomonas pseudoalcaligenes*, *Pseudomonas putida*, *Pseudomonas fluorescens*, and *Comamonas testosteroni*.

Embodiment 9

A method that comprises providing fungi-infested plant with a composition comprising a synergistic ratio of (i) composting bacteria, (ii) bio-surfactant producing bacteria, (iii) bio-remediating bacteria, (iv) bovine feces, and (v) humic acid.

Embodiment 10

The method of embodiment 9, wherein the synergistic ratio is approximately between $10^4$ to $10^{12}$ colony-forming units (CFU) per ml for each bacterial species, approximately between 1% and 25% (w/v) bovine feces, and approximately between 0.01% and 1.00% (w/v) humic acid.

Embodiment 11

The method of embodiment 9, wherein the synergistic ratio is approximately between $10^6$ and $10^{10}$ CFU per ml for each bacterial species, approximately between 5% and 15% (w/v) bovine feces, and approximately between 0.1% and 0.75% (w/v) humic acid.

Embodiment 12

The method of embodiment 9, wherein the synergistic ratio is approximately $10^8$ CFU per ml for each bacterial species, approximately 10% (w/v) bovine feces, and approximately 0.5% (w/v) humic acid.

Embodiment 13

The method of embodiment 9, wherein the composting bacteria comprise *Nocardioides kongjuensis*, *Clostridium phytofermentans*, *Clostridium cellulolyticum*, *Comamonas jiangduensis*, *Comamonas testosteroni*, and *Bacillus subtilis*.

Embodiment 14

The method of embodiment 9, wherein the bio-surfactant producing bacteria comprise *Comamonas jiangduensis*, *Comamonas testosteroni*, and *Pseudomonas aeruginosa*.

Embodiment 15

The method of embodiment 9, wherein the toxin remediating bacteria comprise *Pseudomonas pseudoalcaligenes*, *Pseudomonas putida*, *Pseudomonas fluorescens*, and *Comamonas testosteroni*.

Embodiment 16

The method of embodiment 9, wherein the composting bacteria comprise *Nocardioides kongjuensis*, *Clostridium phytofermentans*, *Clostridium cellulolyticum*, *Comamonas jiangduensis*, *Comamonas testosteroni*, and *Bacillus subtilis*; the bio-surfactant producing bacteria comprise *Comamonas jiangduensis*, *Comamonas testosteroni*, and *Pseudomonas aeruginosa*; and the toxin remediating bacteria comprise *Pseudomonas pseudoalcaligenes*, *Pseudomonas putida*, *Pseudomonas fluorescens*, and *Comamonas testosteroni*.

Embodiment 17

The method of embodiment 9, wherein the plant is turf grass.

Embodiment 18

The method of embodiment 9, wherein the composition is provided to a plant or a plant part, or to the proximity thereof.

Embodiment 19

A method of improving plant health, said method comprising providing plant growth substrate with a composition comprising a synergistic ratio of composting bacteria, bovine feces, and humic acid, wherein the composition improves health of a fungi-infested plant that grows on said plant growth substrate.

Embodiment 20

The method of embodiment 19, wherein the synergistic ratio is approximately between $10^4$ to $10^{12}$ colony-forming units (CFU) per ml for each bacterial species, approximately between 1% and 25% (w/v) bovine feces, and approximately between 0.01% and 1.00% (w/v) humic acid.

Embodiment 21

The method of embodiment 19, wherein the synergistic ratio is approximately between $10^6$ and $10^{10}$ CFU per ml for each bacterial species, approximately between 5% and 15% (w/v) bovine feces, and approximately between 0.1% and 0.75% (w/v) humic acid.

Embodiment 22

The method of embodiment 19, wherein the synergistic ratio is approximately $10^8$ CFU per ml for each bacterial species, approximately 10% (w/v) bovine feces, and approximately 0.5% (w/v) humic acid.

Embodiment 23

The method of embodiment 19, wherein the composting bacteria comprise *Nocardioides kongjuensis*, *Clostridium phytofermentans*, *Clostridium cellulolyticum*, *Comamonas jiangduensis*, *Comamonas testosteroni*, and *Bacillus subtilis*.

Embodiment 24

The method of embodiment 19, wherein the bio-surfactant producing bacteria comprise *Comamonas jiangduensis*, *Comamonas testosteroni*, and *Pseudomonas aeruginosa*.

Embodiment 25

The method of embodiment 19, wherein the toxin remediating bacteria comprise *Pseudomonas pseudoalcaligenes*, *Pseudomonas putida*, *Pseudomonas fluorescens*, and *Comamonas testosteroni*.

Embodiment 26

The method of embodiment 19, wherein the composting bacteria comprise *Nocardioides kongjuensis*, *Clostridium phytofermentans*, *Clostridium cellulolyticum*, *Comamonas jiangduensis*, *Comamonas testosteroni*, and *Bacillus subtilis*; the bio-surfactant producing bacteria comprise *Comamonas jiangduensis*, *Comamonas testosteroni*, and *Pseudomonas aeruginosa*; and the toxin remediating bacteria comprise *Pseudomonas pseudoalcaligenes*, *Pseudomonas putida*, *Pseudomonas fluorescens*, and *Comamonas testosteroni*.

Embodiment 27

The method of embodiment 19, wherein the plant is turf grass.

Examples

Example 1

The composition of the present invention was tested at the North Carolina State University (NCSU) USGA-sanctioned turf-grass testing facility. The composition when applied alone is as effective at reducing *Rhizoctonia* (brown patch) infection as the major commercially available toxic fungicide (Daconil plus Chipco Signature).

TABLE 1

Exemplary typical concentrations of bacteria in final product

| Type of bacteria | Concentration in the composition |
|---|---|
| *Acinetobacter* sp. | $5.0 \times 10^6$ CFU ml$^{-1}$ |
| *Pseudomonas plecoglossicida* | $5.0 \times 10^5$ CFU ml$^{-1}$ |
| *Comamonas testosteroni* | $5.0 \times 10^5$ CFU ml$^{-1}$ |
| *Comamonas jiangduensis* | $5.0 \times 10^5$ CFU ml$^{-1}$ |

Example 2

One embodiment of the composition of the present invention includes: (i) solution of composting bacteria, bio-surfactant producing bacteria, and bio-remediating bacteria composting bacteria, approximately $10^6$-$10^{10}$ CFU per ml for each required bacterial species; (ii) bovine feces, approximately 100 kg dry matter; (iii) humic acid, approximately 5 kg; and (iv) water up to 1,000 liters. It is for example possible to use so-called composting solutions, to obtain a batch of bacteria, use some and then dilute it back to the original volume, wait for bacteria to regrow then use more—and so on.

The above mixture is incubated approximately eight weeks at temperatures of approximately 20° C. After incubation, the mixture is filtered, using a strainer to remove particulate material, which would otherwise block the spraying apparatus, to obtain the composition of the present invention.

The filtered composition is diluted with water, at a 1:15 ratio (i.e., 4 liters of the filtered composition is mixed with 60 liters of tap water. This yields working solution, which may be used immediately, i.e., applied for example by spraying approximately 20 liters of the working solution per area of approximately 3 acres.

Frequency of application is preferably once a week for four weeks or until the turf has regained full health, and every four weeks thereafter. However, the frequency of application may be increased or decreased on a need basis.

Some of the ingredients (e.g., bacteria) can be obtained from various commercially available bacterial composting solutions. Because these compositions are typically considered environmentally friendly and non-toxic to humans, the compositions and methods of the present invention also provide a so-called biological reduction of fungal infestation, i.e., control of fungal infestation without the use toxic fungicides.

Bovine feces useful in the practice of the invention can be obtained from a variety of sources. In one preferred embodiment, the bovine feces is cow dung. For example, bovine feces can be obtained preferably from the feeding pens of free range, non-antibiotic fed cattle. Using cow dung from several animals not fed antibiotics maximizes the array of useful bacteria in the cow dung. Accordingly, a preferred embodiment of the present invention is directed to the use of bovine feces in the form of cow dung obtained from cows that have not been fed antibiotics. One skilled in the art will know that other types of animal dung may be useful in the practice of the present invention, for example dung from individual animals, dung from animals fed antibiotics, and dung from ruminants other than cows. Accordingly, "bovine feces", as used herein, is used to refer to dung obtained from cows and from other cattle.

Humic acid useful in the practice of the present invention can be obtained in a variety of ways. For example, humic acid can be extracted from a humus-rich soil sample, from peat moss, or from humic compost. The most efficient way is to use various commercial products based on leonardite, the naturally occurring deposits of humic acid and fulvic acid. For the purposes of this invention the humic/fulvic acid mixture should be soluble or at least miscible and may be the free acid or the $K^+$ or $Mg^{++}$ salts.

It is to be understood that this invention is not limited to the particular devices, methodology, protocols, subjects, or reagents described, and as such may vary. It is also to be understood that the terminology used herein is for the purpose of describing particular embodiments only, and is not intended to limit the scope of the present invention, which is limited only by the claims. Other suitable modifications and adaptations of a variety of conditions and parameters normally encountered in the fields of fungicides and treatments of plants and soil, obvious to those skilled in the art, are within the scope of this invention. All publications, patents, and patent applications cited herein are incorporated by reference in their entirety for all purposes.

What is claimed is:

1. A composition for improving plant health, the composition comprising a synergistic ratio of (i) composting bacteria, (ii) bio-surfactant producing bacteria, (iii) toxin remediating bacteria, (iv) bovine feces, and (v) humic acid, wherein the composting bacteria comprise at least three of *Nocardioides kongjuensis, Clostridium phytofermentans, Clostridium cellulolyticum, Comamonas jiangduensis,* and *Bacillus subtilis*, the bio-surfactant producing bacteria comprise at least one of *Comamonas jiangduensis* and *Pseudomonas aeruginosa*, and the toxin remediating bacteria comprise at least one of *Pseudomonas pseudoalcaligenes, Pseudomonas putida, Pseudomonas fluorescens,* and *Comamonas testosteroni*, and wherein the synergistic ratio is approximately between $10^4$ to $10^{12}$ colony-forming units (CFU) per ml for each bacterial species, approximately between 1% and 25% (w/v) bovine feces, and approximately between 0.01% and 1.00% (w/v) humic acid.

2. The composition of claim 1, wherein the synergistic ratio is approximately between $10^6$ and $10^{10}$ CFU per ml for each bacterial species, approximately between 5% and 15% (w/v) bovine feces, and approximately between 0.1% and 0.75% (w/v) humic acid.

3. The composition of claim 1, wherein the synergistic ratio is approximately $10^8$ CFU per ml for each bacterial species, approximately 10% (w/v) bovine feces, and approximately 0.5% (w/v) humic acid.

4. A method that comprises providing fungi-infested plant with a composition comprising a synergistic ratio of (i) composting bacteria, (ii) bio-surfactant producing bacteria, (iii) toxin remediating bacteria, (iv) bovine feces, and (v) humic wherein the composting bacteria comprise at least three of *Nocardioides kongjuensis, Clostridium phytofermentans, Clostridium cellulolyticum, Comamonas jiangduensis,* and *Bacillus subtilis*, the bio-surfactant producing bacteria comprise at least one of *Comamonas jiangduensis* and *Pseudomonas aeruginosa*, and the toxin remediating bacteria comprise at least one of *Pseudomonas pseudoalcaligenes, Pseudomonas putida, Pseudomonas fluorescens,* and *Comamonas testosteroni*, and wherein the synergistic ratio is approximately between $10^4$ to $10^{12}$ colony-forming units (CFU) per ml for each bacterial species, approximately between 1% and 25% (w/v) bovine feces, and approximately between 0.01% and 1.00% (w/v) humic acid.

5. The method of claim 4, wherein the synergistic ratio is approximately between $10^6$ and $10^{10}$ CFU per ml for each bacterial species, approximately between 5% and 15% (w/v) bovine feces, and approximately between 0.1% and 0.75% (w/v) humic acid.

6. The method of claim 4, wherein the synergistic ratio is approximately $10^8$ CFU per ml for each bacterial species, approximately 10% (w/v) bovine feces, and approximately 0.5% (w/v) humic acid.

7. The method of claim 4, wherein the plant is turf grass.

8. The method 4, wherein the composition is provided to a plant or a plant part, or to the proximity thereof.

9. A method of improving plant health, said method comprising providing plant growth substrate with a composition comprising a synergistic ratio of composting bacteria, bio-surfactant producing bacteria, toxin remediating bacteria, bovine feces, and humic acid, wherein the composition improves health of a fungi-infested plant that grows on said plant growth substrate, wherein the composting bacteria comprise at least three of *Nocardioides kongjuensis, Clostridium phytofermentans, Clostridium cellulolyticum, Comamonas jiangduensis,* and *Bacillus subtilis*, the bio-surfactant producing bacteria comprise at least one of *Comamonas jiangduensis* and *Pseudomonas aeruginosa*, and the toxin remediating bacteria comprise at least one of *Pseudomonas pseudoalcaligenes, Pseudomonas putida, Pseudomonas fluorescens,* and *Comamonas testosteroni*, and wherein the synergistic ratio is approximately between $10^4$ to $10^{12}$ colony-forming units (CFU) per ml for each bacterial species, approximately between 1% and 25% (w/v) bovine feces, and approximately between 0.01% and 1.00% (w/v) humic acid.

10. The method of claim 9, wherein the synergistic ratio is approximately between $10^6$ and $10^{10}$ CFU per ml for each bacterial species, approximately between 5% and 15% (w/v) bovine feces, and approximately between 0.1% and 0.75% (w/v) humic acid.

11. The method of claim 9, wherein the synergistic ratio is approximately $10^8$ CFU per ml for each bacterial species, approximately 10% (w/v) bovine feces, and approximately 0.5% (w/v) humic acid.

12. The method of claim 9, wherein the plant is turf grass.

* * * * *

UNITED STATES PATENT AND TRADEMARK OFFICE
CERTIFICATE OF CORRECTION

PATENT NO. : 10,051,869 B2
APPLICATION NO. : 14/756088
DATED : August 21, 2018
INVENTOR(S) : Gregory R. H. Smith and Eric Davies Page 1 of 1

It is certified that error appears in the above-identified patent and that said Letters Patent is hereby corrected as shown below:

In the Claims

Column 18, Claim 4, Line 9 should read:
humic acid, wherein the composting bacteria comprise at least Signed and Sealed this
Nineteenth Day of February, 2019

Andrei Iancu
*Director of the United States Patent and Trademark Office*